United States Patent [19]
Pedersen et al.

[11] Patent Number: 5,916,168
[45] Date of Patent: Jun. 29, 1999

[54] THREE DIMENSIONAL M-MODE ULTRASONIC DIAGNOSTIC IMAGING SYSTEM

[75] Inventors: Robert H. Pedersen, Woodinville; Patrick René Pesque, Bothell, both of Wash.

[73] Assignee: Advanced Technology Laboratories, Inc., Bothell, Wash.

[21] Appl. No.: 08/858,172

[22] Filed: May 29, 1997

[51] Int. Cl.⁶ ........................................ A61B 8/00
[52] U.S. Cl. ............................. 600/443; 128/916
[58] Field of Search .................. 128/916; 600/443, 600/450

[56] References Cited

U.S. PATENT DOCUMENTS

| | | | |
|---|---|---|---|
| 5,099,847 | 3/1992 | Powers et al. | 128/660.07 |
| 5,282,471 | 2/1994 | Sato | 128/916 |
| 5,353,220 | 10/1994 | Ito et al. | 128/916 |
| 5,415,171 | 5/1995 | Goh et al. | 600/443 |
| 5,435,310 | 7/1995 | Sheehan et al. | 600/443 |
| 5,454,371 | 10/1995 | Fenster et al. | 600/443 |
| 5,465,721 | 11/1995 | Kishimoto et al. | 128/916 |
| 5,474,073 | 12/1995 | Schwartz et al. | 128/661.1 |
| 5,601,084 | 2/1997 | Sheehan et al. | 600/443 |
| 5,709,210 | 1/1998 | Green et al. | 600/443 |

OTHER PUBLICATIONS

"Anatomical M–Mode (Virtual, VarioPlane, Anyplane M–Mode)" by James V. Chapman (1997).

*Primary Examiner*—Marvin M. Lateef
*Assistant Examiner*—Maulin Patel
*Attorney, Agent, or Firm*—W. Brinton Yorks, Jr.

[57] ABSTRACT

A three dimensional M-mode imaging system and techniques are described for acquiring and forming three dimensional ultrasonic M-mode images from ultrasonic data acquired over time from a stationary scanhead. The resultant images exhibit two spatial dimensions and one temporal dimension.

42 Claims, 3 Drawing Sheets

THREE DIMENSIONAL M-MODE ULTRASONIC DIAGNOSTIC IMAGING SYSTEM

This invention relates to ultrasonic diagnostic imaging systems and, in particular, to three dimensional ultrasonic M-mode imaging One of the primary uses of medical diagnostic ultrasound is the diagnosis of cardiac function and disease. Echocardiography revolves around the functioning of the heart and the diagnosis of abnormal conditions of cardiac performance and pathology. Of significant interest to the cardiologist in making these diagnoses is clear delineation of the heart structure itself, and in particular the motion of the well-defined heart muscle as it cyclically pumps blood.

An early ultrasound technique for visualizing the dynamics of the beating heart is time-motion or M-mode imaging. An M-mode image is formed by repetitive scanning of a single scanline, termed an A-line, at the same location in the body. The M-mode display is formed by displaying each A-line next to the previously acquired A-line, forming a time sequence of parallel A-lines. The M-mode display was technically easy to accomplish, as there is no need to move or steer the ultrasound beam, and the M-mode display could be simply recorded on a stripchart recorder. Each line in the display would show the instantaneous position of tissue intersecting the beam at that particular moment, and moving tissue such as the heart walls would appear at different locations on the scanlines over time. Thus, the time sequence of A-lines would reveal the movement of tissue intersecting the A-line location and was useful in cardiac diagnosis. Of course, the M-mode image only disclosed information about the location of the one-dimensional A-line. To examine any other line through the heart, it was necessary to relocate the transducer and wait while another time sequence of A-lines is acquired and displayed from the new beam location. It would be desirable to be able to quickly and comprehensively acquired M-mode information over a significant portion of the heart or other regions of the body where motion is relevant to diagnosis without the painstaking process of repetitive M-mode acquisitions. Furthermore, it would be desirable to have a diagnostic technique which makes use of such comprehensive information in a single display.

In accordance with the principles of the present invention, apparatus and techniques are presented for three dimensional M-mode imaging. A three dimensional M-mode display is unlike conventional three dimensional ultrasound displays in that two of the dimensions of the display are spatial and the third is temporal. The three dimensional M-mode display brings the equivalent of all of the information of numerous conventional M-mode scans to bear in a single ultrasound image.

In the drawings:

FIG. 1a illustrates a modification of the system of FIG. 1 for performing three dimensional Doppler M-mode imaging;

Figure 1:
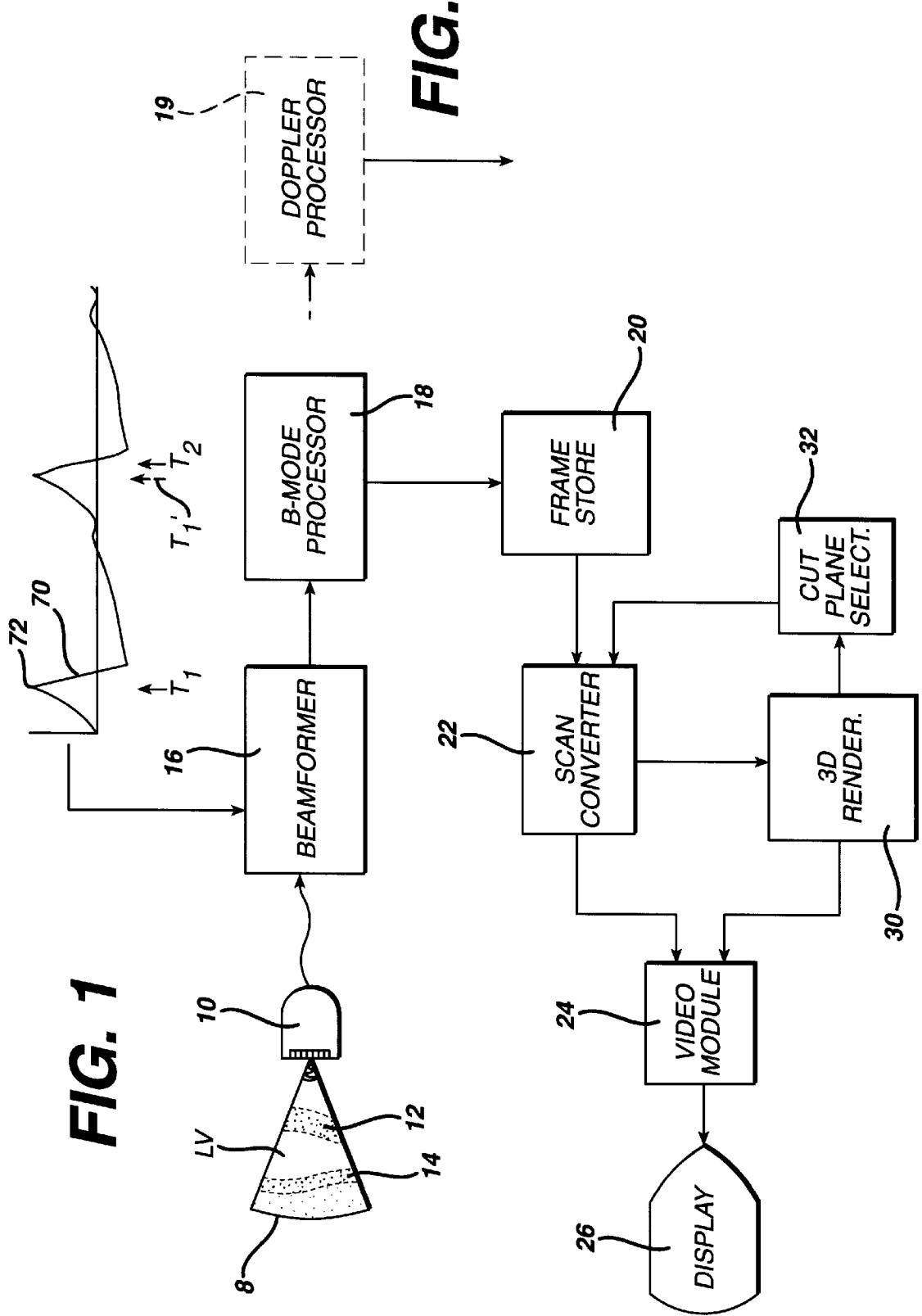
FIG. 1 is a block diagram of an ultrasonic imaging system which performs three dimensional M-mode imaging in accordance with the principles of the present invention.

Referring first to FIG. 1, an ultrasonic imaging system constructed in accordance with the principles of the present invention is shown in block diagram form. A scanhead 10 includes a transducer for scanning a region of the body. In this particular example the scanhead includes a phased array transducer which is scanning a sector-shaped region 8 of the body which includes a section of the heart. The features of the heart shown in the sector 8 include a portion of the left ventricle (LV), a septum 12 separating the left and right ventricles, and the posterior wall 14. While a phase array transducer is generally preferred for cardiac scanning, the present invention can be practiced with any two dimensional scanning transducer such as linear arrays, curved arrays, and mechanical sector scanners with single piston or annular array transducers.

The scanhead 10 is coupled to a beamformer when the transducer used is an array transducer, which steers and/or focuses the transducer beams. Ultrasonic echo signals produced by the beamformer are coupled to a B-mode processor which processes the echo signals for display as B-mode or greyscale echo information.

The B-mode signals are stored in frame store 20 as frames of image information. If it is necessary or desirable to convert the spatial coordinates of the B-mode signals to a different coordinate system, such as the conversion of polar coordinates to Cartesian coordinates, the signals are scan converted in a scan converter 22. B-mode signals from a linear array are already in a rectilinear coordinate orientation and may need no coordinate conversion. The image frames may then be converted to appropriate video drive signals by a video module 24 and displayed on an image display 26.

In accordance with the principles of the present invention, the B-mode signals may also be rendered to form a three dimensional image by 3D rendering processor 30. The 3D rendering processor may operate on the B-mode data to form a three dimensional image in a number of ways. When the B-mode data has been acquired in the form of a sequence of two dimensional images covering the volumetric region of interest, the image set may be processed for three dimensional presentation by relocating points in the images in order to present the images as if the scanned region is being viewed from directions other than orthogonal to the image planes. A mathematically precise expression for relocating the image points when viewing the scanned region from different viewpoints in the horizontal plane is:

$$\begin{bmatrix} x' \\ y' \end{bmatrix} = \begin{bmatrix} x\cos(\theta) \\ y \end{bmatrix} + \begin{bmatrix} z\sin(\theta) \\ 0 \end{bmatrix}$$

where θ is the angle of rotation of the image in relation to a reference plane such as a viewing plane orthogonal to the line of sight of a viewer, x, y and z are the coordinates of a point in the original image plane, and x' and y' are the coordinates of the image point after relocation. The z coordinate of a planar image set is the location of each plane in the sequence of planes, and may be obtained by assuming a nominal spacing between image planes or by acquiring a measured spatial coordinate of each plane as described in U.S. Pat. No. 5,474,073. Point relocation when viewing the scanned region from different viewpoints in a vertical direction is expressed by:

$$\begin{bmatrix} X' \\ y' \end{bmatrix} = \begin{bmatrix} X \\ y\cos\theta \end{bmatrix} - \begin{bmatrix} 0 \\ z\sin\theta \end{bmatrix}$$

and point relocation for views of the scanned region as it is rotated about a z axis is performed by the expression:

$$\begin{bmatrix} x' \\ y' \end{bmatrix} = \begin{bmatrix} x\cos\theta - y\sin\theta \\ x\sin\theta + y\cos\theta \end{bmatrix}$$

In this expression θ is the degree of rotation of the planes about a z axis relative to a reference direction.

Figure 6:
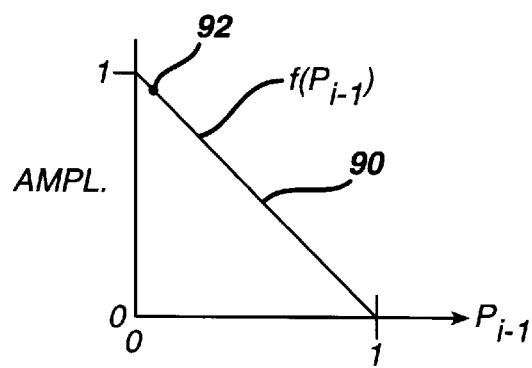
FIG. 6 illustrates an opacity-transparency rendering function suitable for use in an embodiment of the present invention.

The appearance of the three dimensional image can be enhanced by using different rendering techniques such as maximum intensity projection or surface enhancement. The present inventors have found that surface enhancement makes pleasing renderings for images of the present invention. Surface renderings can be produced by processing the data of a three dimensional data set along the vectors of the viewing direction in accordance with:

$$P_{x,y}(\theta) = \sum_{i=1}^{N} f(P_1 \ldots P_{i-1})P_i$$

where $P_{x,y}(\theta)$ is an image point at x,y coordinates in a three dimensional image viewed at angle θ to the data set. The function $f(P_1 \ldots P_{i-1})$ is an opacity-transparency function which is used as a rendering parameter as described in U.S. Pat. No. 5,720,291 which is a function of points encountered along the viewing direction vector. As an example, the opacity-transparency function can simply be a function of the immediately preceding pixel, that is, $f(P_{i-1})$. When the function is inversely related to the pixel value as shown by the transfer characteristic of FIG. 6, the rendering of cardiac data will emphasize the endocardial wall. When the viewing vector traverses the chamber of the heart with only low level echo returns from blood, the rendering process will produce results of near zero due to the low level echo values. When the first significant echo from the endocardial wall is encountered, which may exhibit a level approaching a normalized value of 1, the near zero value of the preceding pixel of the blood pool will cause the opacity-transparency function to have a value approaching 1 as illustrated by point 92 on the function curve 90 of FIG. 6, and the product of the two will approach one. The opacity-transparency function will have lesser values as the process continues into the tissue of the cardiac wall due to the increased amplitudes of the echo signals from the tissue.

A maximum intensity projection can be produced by rendering the data set in accordance with the expression $$P_{x,y}(\theta) = \operatorname*{Max}_{i=1,N}[P_i]$$

and a mean intensity projection can be produced by rendering the data set in accordance with the expression $$P_{x,y}(\theta) = (1/N)\sum_{i=1}^{N} P_i$$

Other rendering algorithms, such as those utilizing surface segmentation or object shape recognition may also be employed as desired. The three dimensional rendering is converted to video signals by the video module 24 and shown on the display 26.

When the scanhead is swept across the skin as taught in U.S. Pat. No. 5,474,073 a volumetric region of the body is scanned by consecutively produced image planes. The echo information of these image planes provides the three dimensional data set which is used by the three dimensional rendering processor 30 to render a three dimensional image of the volumetric region. Each data point on each image plane has an x,y,z address location in the volumetric region; thus each data point has its own unique spatial address in the volumetric region. Conventionally the x,y address values relate to x,y position on an image plane, and the z value relates to the location of the image plane in the sequence of image planes.

However, in accordance with the principles of the present invention, the three dimensional data set is acquired over time from the same planar region of the body. This may be done, for instance, by holding the scanhead 10 in one position in relation to the region of interest, then acquiring a sequence of image planes. Each data point on each image plane has an x,y,z address for three dimensional rendering: two spatial and one temporal. For example, x and y can relate to x,y position on an image plane, and the z value relates to the time of acquisition of the image plane in the sequence of image planes.

Figure 2:
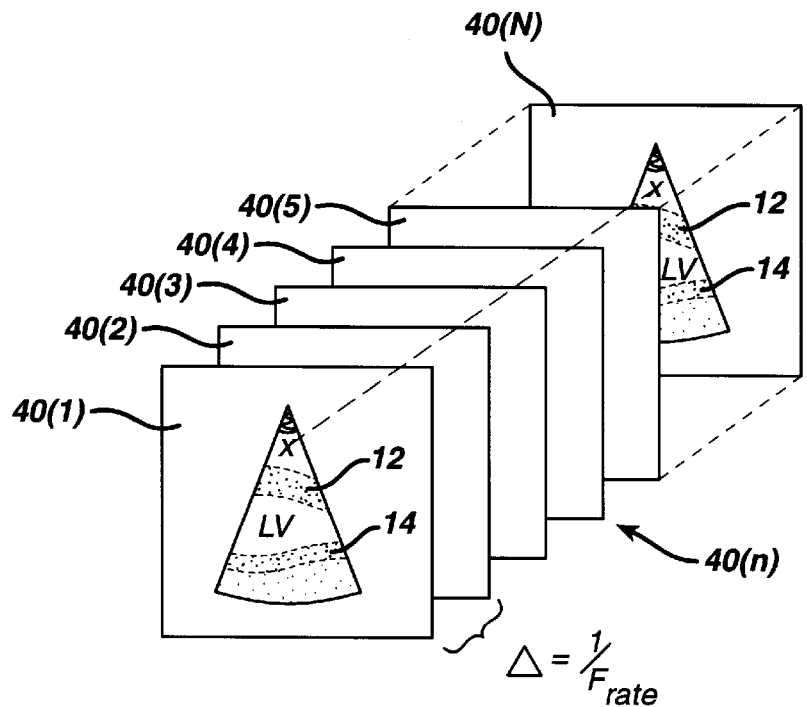
FIG. 2 shows a sequence of images which are being used to render a three dimensional display.

FIG. 2 shows an image set 40(n) acquired in accordance with the principles of the present invention. Each image is of the left ventricular region of the image 8 of FIG. 1. The number in parenthesis of the reference numeral for each image indicates the order of its acquisition relative to the other images. Thus, image 40(2) was acquired after image 40(1) and before image 40(3). In this example the left ventricular image set comprises one hundred images (n=100), and was acquired at the frame rate of 100 frames per second. This provides a temporal frame to frame spacing value of $\Delta=1/F_{rate}$. Thus, each data point in the image set has a three dimensional address of x,y,z where x and y are the x,y locations on a particular image frame and z is the temporal position of the frame nΔ in the time sequence of frames.

Figure 3:
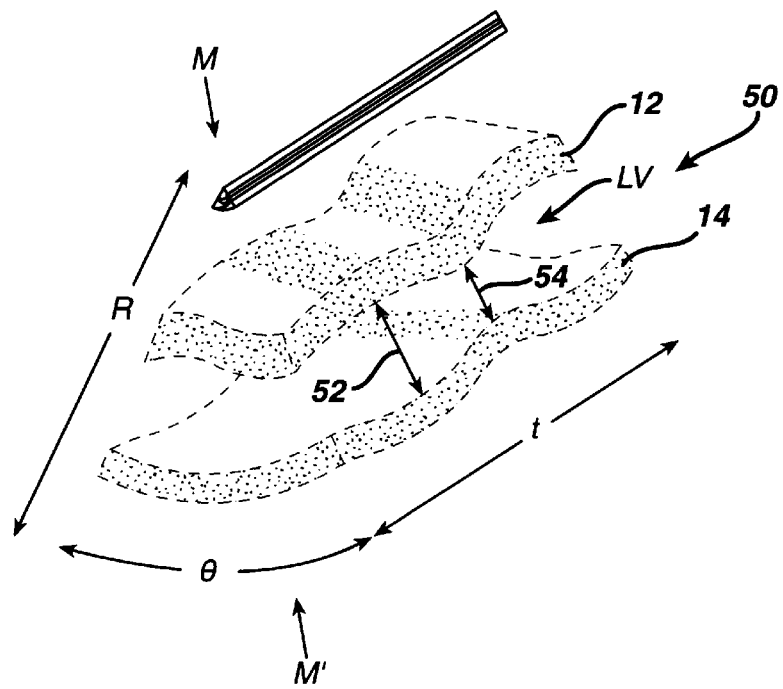
FIG. 3 illustrates a three dimensional M-mode display of the present invention.

When the three dimensional data set of the frame sequence is processed by the three dimensional rendering processor 30, a three dimensional image 50 such as that shown in FIG. 3 is produced. The 3D image 50 has been rotated about both the x and y axes with respect to a view normal to the front image plane in the sequence of images. The 3D image 50 shows the septum 12 and the posterior wall 14 in three dimensions, two spatial and one temporal. As the dimensional arrows around the image show, the two spatial dimensions are R and θ, and the temporal dimension is t.

The inventors refer to the image 50 as a three dimensional M-mode image because the undulations in the image illustrate the motion of the septum and posterior wall as the heart contracts and expands during the heartbeat cycle. The 3D image 50 shows that the septum and posterior wall of the left ventricle have moved relatively far apart when the heart is relaxed (expanded), as shown by the arrow 52 in FIG. 3. This dimension can be quantitatively measured, if desired and, unlike a conventional M-mode image, the dimension can be measured between any two dimensional points of the septum and posterior wall due to the three dimensional nature of the image 50. Similarly, measurements can be taken when the heart is contracted and the septum 12 and posterior wall 14 are relatively close together, as shown by the arrow 54 in FIG. 3.

Figure 4:
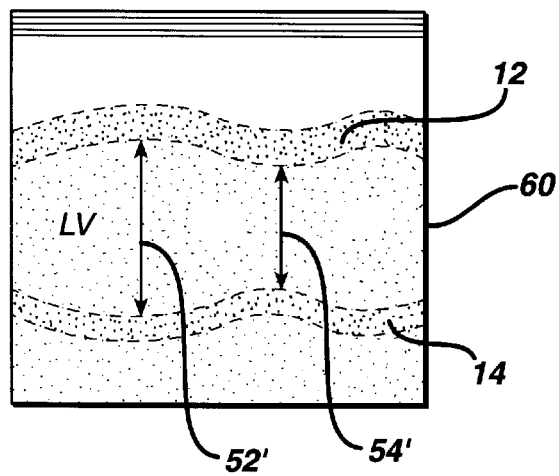
FIG. 4 illustrates a two dimensional M-mode display formed by cut plane M–M' of FIG. 3.

The cut plane selector 32 of FIG. 1 can be used to form a conventional M-mode image from the image data set of FIGS. 2 or 3. The user can manipulate an M-mode cursor over the 3D image 50 (or one of the images of FIG. 2) as, for example, locating an M-mode cursor between the arrows M–M' in FIG. 3. The cut plane selector 32 will then select the same A-line from each image plane in the temporal dimension and assemble a two dimensional M-mode image in the plane of the A-lines. Such an M-mode image 60 is shown in FIG. 4. Measurements 52' and 54' can be made on this planar image between the septum 12 and the posterior wall 14 as shown in FIG. 4.

Quantified measurements on the three dimensional M-mode images of the present invention, such as indicated by the arrows 50 and 52 in FIG. 3, can be assisted by tracing the tissue borders on the images, then measuring from the borders delineated by the tracings. A preferred technique for tracing borders in temporally acquired ultrasonic images such as those of the present invention is described in U.S. Pat. application Ser. No. 08/865,340, in which velocity data is used to assist in the tracing of moving tissue in the body.

The three dimensional M-mode images of the present invention can formed by any ultrasound acquisition technique. While conventional greyscale acquisition can be used for B-mode images, the present inventors have found it to be advantageous to use harmonic B-mode for three dimensional M-mode imaging. In harmonic B-mode imaging, the ultrasonic waves transmitted into the body have a fundamental frequency, but reception of echoes is done at a harmonic of the fundamental frequency. A system which performs harmonic reception is shown in U.S. Pat. [application Ser. No. 08/723,483]. The higher order reception frequency has been found to produce clearer, more sharply defined images in cases where the beam direction is substantially parallel to a tissue surface in the image, surfaces where the scattering angle is generally viewed as being suboptimal in conventional B-mode imaging. Another B-mode technique which is useful for three dimensional M-mode imaging is power motion imaging, as described in U.S. Pat. No. 5,718,229.

Three dimensional Doppler M-mode imaging can also be employed, as shown in FIGS. 1 and 1a. FIG. 1a illustrates the processing of received echo signals by a Doppler processor 19 to produce Doppler image data representing velocity, intensity, variance, or some other Doppler characteristic. The image set of FIG. 2 then comprises Doppler data instead of or in addition to the B-mode information described above. Three dimensional Doppler M-mode images are then rendered by the three dimensional rendering processor 30 from the Doppler (or Doppler and B-mode) data set. A three dimensional M-mode image can be formed by colorflow images acquired from a planar region of the body, for instance.

When moving tissue such as the heart is to be rendered in a three dimensional M-mode image, one technique which may be employed is to discriminate for such motion by acquiring and processing color Doppler information at large amplitude and low frequencies from the tissue. Such Color Doppler information is temporally acquired then rendered to form a three dimensional M-mode image in accordance with the techniques described herein.

Figure 5:
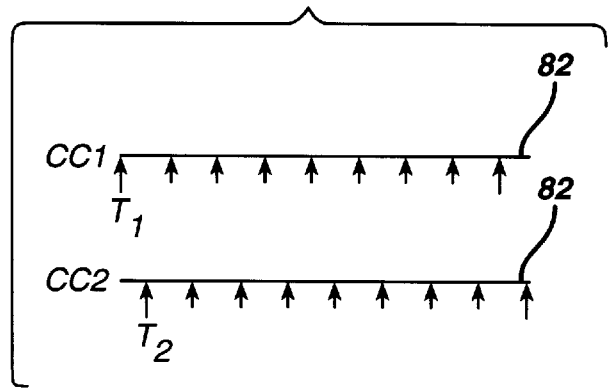
FIG. 5 illustrates an acquisition timing sequence for increasing the information density of a three dimensional M-mode display.

When practicing the present invention through the acquisition of planar images, it is generally desirable to acquire the images as rapidly as possible, so that the resolution in the temporal dimension will be as high as possible. FIGS. 1 and 5 illustrate a technique for affording this high temporal resolution. The beamformer 16 is gated to acquire images in timed relationship to a QRS heart waveform 70. This gating waveform can be acquired by an ECG sensor which senses the heartbeat and produces the QRS waveform. A first sequence of image frames is acquired in a given phase relationship to the cardiac cycle as shown by the QRS waveform 70 and the frame acquisition timing sequence of FIG. 5. In the illustrated example a time marker $T_1$ is produced at the peak 72 of the QRS waveform, as shown in both drawings. The arrows along the timeline 82 in FIG. 5 illustrate the acquisition times of image frames separated by uniform intervals and following the time marker $T_1$ during a first cardiac cycle CC1.

During a subsequent cardiac cycle which begins with the same time marker, $T_1'$ in FIG. 1, images are acquired separated by the same uniform intervals, but starting from a time marker $T_2$, which is offset from $T_1'$ by half of the separation interval. Thus, the frames acquired during this second cardiac cycle CC2 are interleaved in the phases of the heart cycle between the phases of the first cardiac cycle, as illustrated by the relative positions of the acquisition timing arrows of cardiac cycles CC1 and CC2 in FIG. 5. The acquired frames, when interleaved in their relative phase relationships, thus comprise a greater sampling density in the temporal dimension than either sequence individually. A three dimensional rendering of the interleaved data set will provide a highly resolved three dimensional M-mode image.

Variations of phase varying acquisition will readily occur to those skilled in the art. For instance if the heart cycle is irregular, it may be preferable to acquire one image each heart cycle and slip the acquisition time to a later phase in the cycle with each heartbeat. The sequence of images acquired would thus represent images of the heart at successively later phases with reference to the chosen QRS trigger point. Further details on such variations may be found in U.S. Pat. No. 5,099,847.

Various modification can be made to the arrangement of FIG. 1 without departing from the teachings of the present invention, depending upon the environment in which the invention is practiced. For example, scan conversion can be done before the frame store 20. Alternately, scan conversion can be eliminated by having the three dimensional rendering processor 30 operate directly upon the R-θ data of the processor 18,19 without scan conversion. Alternatively, the processed data may have rectilinear coordinates and not require scan conversion. Another alternative is to incorporate the frame store into the three dimensional rendering processor 30, whereby the processor 30 stores the data set upon which it operates. Other modifications will occur to those skilled in the art.

what is claimed is:

1. An ultrasonic diagnostic imaging system comprising:
   a transducer for receiving ultrasonic echo information from a region of the body; and
   a processor, responsive to said ultrasonic echo information, to produce a three dimensional display of said information,
   wherein two of the dimensions of said three dimensional display are spatial and the third dimension is temporal.

2. An ultrasonic diagnostic imaging system for providing three dimensional M-mode images comprising:
   a scanhead for acquiring sequential planes of echo information from a planar region of the body;
   a processor for processing said echo information to produce a sequence of B-mode or Doppler images; and
   a three dimensional rendering processor which produces a three dimensional image of said images as a function of their temporal displacement.

3. A method of forming a three dimensional M-mode image of moving tissue comprising the steps of:

acquiring and processing color Doppler information at large amplitudes and low frequencies from moving tissue over time; and rendering said color Doppler information to form a three dimensional image presentation wherein two of said dimensions are spatial and the third is temporal.

4. A method of forming a three dimensional M-mode image comprising the steps of:

repetitively acquiring two dimensional ultrasonic images over time of substantially the same planar region of the body;

rendering a three dimensional ultrasonic image from said two dimensional ultrasonic images, wherein two of said three dimensions are spatial dimensions of said planar region and the third dimension is the time of acquisition of said two dimensional images; and displaying said three dimensional ultrasonic image.

5. The method of claim 4, wherein said rendering step renders a three dimensional ultrasonic image by maximum intensity projection.

6. The method of claim 4, wherein said rendering step utilizes surface rendering to produce a three dimensional ultrasonic image.

7. The method of claim 6, wherein said rendering step processes said two dimensional ultrasonic images with an opacity-transparency function.

8. The method of claim 4, wherein said rendering step renders a three dimensional ultrasonic image by mean intensity projection.

9. The method of claim 4, wherein said acquiring step acquired two dimensional ultrasonic image frames, and wherein, in said rendering step, said third dimension is temporal frame to frame spacing.

10. The method of claim 4, further comprising the steps of:

selecting a cut plane of said three dimensional ultrasonic image, which cut plane exhibits said third dimension as one of its dimensions; and displaying said selected cut plane as a two dimensional M-mode image.

11. The method of claim 10, wherein said cut plane comprises a plurality of spatially constant A-lines of said two dimensional images.

12. The method of claim 4, further comprising the step of tracing one or more tissue borders of said three dimensional ultrasonic image.

13. The method of claim 12, further comprising the step of making measurements based upon said tissue border tracings.

14. The method of claim 4, wherein said acquiring step comprises acquiring echoes at a harmonic of a fundamental transmit frequency.

15. The method of claim 4, wherein said acquiring step comprises acquiring two dimensional ultrasonic images in a predetermined phase relationship to a cardiac cycle.

16. The method of claim 15, wherein said acquiring step comprises acquiring two dimensional ultrasonic images in two or more predetermined phase relationships to a cardiac cycle.

17. A method of forming a three dimensional Doppler M-mode image comprising the steps of:

repetitively acquiring Doppler echo signals over time of substantially the same planar region of the body;

processing said Doppler echo signals to produce Doppler image data;

rendering a three dimensional ultrasonic image from said Doppler image data, wherein two of said three dimensions are spatial dimensions of said planar region and the third dimension is the time of acquisition of said Doppler image data; and displaying said three dimensional ultrasonic image.

18. The method of claim 17, wherein said processing step produces Doppler velocity, intensity, or variance image data.

19. The method of claim 17, wherein said processing step produces Doppler image data from large amplitude, low frequency Doppler echo signals.

20. The method of claim 19, wherein said processing step produces Doppler image data of tissue from large amplitude, low frequency Doppler echo signals.

21. The ultrasonic diagnostic imaging system of claim 2, wherein:

said scanhead is operated to repetitively acquire two dimensional ultrasonic images over time of substantially the same planar region of the body;

said three dimensional rendering processor renders a three dimensional ultrasonic image from two dimensional ultrasonic image data, wherein two of said three dimensions are spatial dimensions depicted by said image data and the third dimension is the time of acquisition of said two dimensional image data; and an image display coupled to said three dimensional rendering processor for displaying said three dimensional ultrasonic image; and further comprising:

a storage device, coupled to said echo information processor and said three dimensional rendering processor, for storing said sequence of images in relation to the time sequence of their acquisition.

22. The ultrasonic diagnostic imaging system of claim 2, wherein said three dimensional rendering processor renders a three dimensional ultrasonic image by maximum intensity projection.

23. The ultrasonic diagnostic imaging system of claim 2, wherein said three dimensional rendering processor utilizes surface rendering to produce a three dimensional ultrasonic image.

24. The ultrasonic diagnostic imaging system of claim 23, wherein said three dimensional rendering processor processes said images with an opacity-transparency function.

25. The ultrasonic diagnostic imaging system of claim 2, wherein said three dimensional rendering processor renders a three dimensional ultrasonic image by mean intensity projection.

26. The ultrasonic diagnostic imaging system of claim 21, wherein said storage device stores said images as image frames, and wherein said third dimension is temporal frame to frame spacing.

27. The ultrasonic diagnostic imaging system of claim 21, further comprising:

a cut plane selector which selects a cut plane of said three dimensional image, which cut plane exhibits said third dimension as one of its dimensions; and wherein said selected cut plane is displayed on said image display as a two dimensional M-mode image.

28. The ultrasonic diagnostic imaging system of claim 27, wherein said cut plane comprises a plurality of spatially constant A-lines of said two dimensional images.

29. The ultrasonic diagnostic imaging system of claim 2, further comprising an image tracer for tracing one or more tissue borders of said three dimensional image.

30. The ultrasonic diagnostic imaging system of claim 29, further comprising means for making measurements based upon said tissue border tracings.

31. The ultrasonic diagnostic imaging system of claim 2, further comprising a receiver, coupled to said scanhead, for acquiring echoes at a harmonic of a fundamental transmit frequency; and wherein said echo information processor produces harmonic ultrasonic image data.

32. The ultrasonic diagnostic imaging system of claim 2, further comprising a scanhead controller, coupled to said scanhead, for acquiring two dimensional ultrasonic image echo information in a predetermined phase relationship to a cardiac cycle.

33. The ultrasonic diagnostic imaging system of claim 32, wherein said scanhead controller controls said scanhead to acquire two dimensional ultrasonic image echo information in two or more predetermined phase relationships to a cardiac cycle.

34. The ultrasonic diagnostic imaging system of claim 32, wherein said scanhead controller includes an ECG sensor.

35. An ultrasonic diagnostic imaging system which produces three dimensional Doppler M-mode images comprising:
   an ultrasonic scanhead which is operated to repetitively acquire Doppler echo signals over time of substantially the same planar region of the body;
   a Doppler processor coupled to receive said Doppler echo signals to produce Doppler image data;
   a storage device for storing said Doppler image data in relation to the time sequence of its acquisition;
   a three dimensional image processor which renders a three dimensional ultrasonic image from said Doppler image data, wherein two of said three dimensions are spatial dimensions of said planar region and the third dimension is the time of acquisition of said Doppler image data; and
   an image display for displaying said three dimensional ultrasonic image.

36. The ultrasonic diagnostic imaging system of claim 35, wherein said Doppler processor produces Doppler velocity, intensity, or variance image data.

37. The ultrasonic diagnostic imaging system of claim 35, wherein said Doppler processor produces Doppler image data from large amplitude, low frequency Doppler echo signals.

38. The ultrasonic diagnostic imaging system of claim 1, wherein said transducer is operated to repetitively acquire echo information for two dimensional ultrasonic image frames over time of substantially the same planar region of the body; and
   wherein said two spatial dimensions relate to the spatial dimensions of said ultrasonic image frames and said third dimension relates to the acquisition time of said ultrasonic image frames.

39. The ultrasonic diagnostic imaging system of claim 38, wherein said processor comprises a three dimensional rendering processor which renders a three dimensional ultrasonic image by maximum intensity projection.

40. The ultrasonic diagnostic imaging system of claim 38, wherein said processor comprises a three dimensional rendering processor which utilizes surface rendering to produce a three dimensional ultrasonic image.

41. The ultrasonic diagnostic imaging system of claim 40, wherein said three dimensional rendering processor processes said ultrasonic echo information with an opacity-transparency function.

42. The ultrasonic diagnostic imaging system of claim 38, wherein said processor comprises a three dimensional rendering processor which renders a three dimensional ultrasonic image by mean intensity projection.

* * * * *